United States Patent
Tets et al.

(10) Patent No.: US 11,248,020 B2
(45) Date of Patent: Feb. 15, 2022

(54) OLIGONUCLEOTIDE COMPOSITIONS AND METHODS FOR TREATING DISEASES

(71) Applicants: Viktor Veniaminovich Tets, New York, NY (US); Georgy Viktorovich Tets, New York, NY (US)

(72) Inventors: Viktor Veniaminovich Tets, New York, NY (US); Georgy Viktorovich Tets, New York, NY (US)

(73) Assignees: Viktor Veniaminovich Tets, St. Petersburg (RU); Georgy Viktorovich Tets, St. Petersburg (RU)

( * ) Notice: Subject to any disclaimer, the term of this patent is extended or adjusted under 35 U.S.C. 154(b) by 73 days.

(21) Appl. No.: 16/615,966

(22) PCT Filed: May 22, 2018

(86) PCT No.: PCT/US2018/033900
§ 371 (c)(1),
(2) Date: Nov. 22, 2019

(87) PCT Pub. No.: WO2018/217756
PCT Pub. Date: Nov. 29, 2018

(65) Prior Publication Data
US 2020/0277324 A1    Sep. 3, 2020

Related U.S. Application Data

(60) Provisional application No. 62/510,461, filed on May 24, 2017.

(51) Int. Cl.
| | | |
|---|---|---|
| *C07H 21/00* | (2006.01) |
| *A61P 9/10* | (2006.01) |
| *A61P 25/28* | (2006.01) |
| *A61P 37/06* | (2006.01) |
| *A61P 35/00* | (2006.01) |
| *C07H 21/04* | (2006.01) |
| *A61K 31/711* | (2006.01) |
| *A61K 31/7084* | (2006.01) |
| *A61K 31/7105* | (2006.01) |
| *A61K 31/7052* | (2006.01) |
| *A61K 31/7088* | (2006.01) |
| *A61K 31/7068* | (2006.01) |
| *A61K 31/708* | (2006.01) |
| *A61K 31/7076* | (2006.01) |
| *A61K 31/7072* | (2006.01) |
| *C07H 21/02* | (2006.01) |

(52) U.S. Cl.
CPC ............ *C07H 21/00* (2013.01); *A61K 31/708* (2013.01); *A61K 31/7052* (2013.01); *A61K 31/7068* (2013.01); *A61K 31/7072* (2013.01); *A61K 31/7076* (2013.01); *A61K 31/7084* (2013.01); *A61K 31/7088* (2013.01); *A61K 31/711* (2013.01); *A61K 31/7105* (2013.01); *A61P 9/10* (2018.01); *A61P 25/28* (2018.01); *A61P 35/00* (2018.01); *A61P 37/06* (2018.01); *C07H 21/02* (2013.01); *C07H 21/04* (2013.01)

(58) Field of Classification Search
None
See application file for complete search history.

(56) References Cited

U.S. PATENT DOCUMENTS

| | | | |
|---|---|---|---|
| 9,950,002 B2 * | 4/2018 | Kandimalla | ....... A61K 51/1244 |
| 2009/0012023 A1 | 1/2009 | Hecker et al. | |
| 2014/0056892 A1 | 2/2014 | Noelle et al. | |
| 2015/0089681 A1 | 3/2015 | Van Der Oost et al. | |

FOREIGN PATENT DOCUMENTS

| | | | |
|---|---|---|---|
| WO | 2003/022255 A2 | 3/2003 | |
| WO | 2009/067243 A2 | 5/2009 | |
| WO | WO2018/096538 | * 5/2018 | ........... A61K 31/277 |

OTHER PUBLICATIONS

Koji et al., "Preparations of Histone and Nucleosome" J Fac Agr Kyushu Univ vol. 22 pp. 2013-2210 (Year: 1978).*
Jones et al., "The Role of DNA Methylation in Mammalian Epigenetics" Science vol. 293 pp. 1068-1070 (Year: 2001).*
Abdul-Sater et al., "The overlapping host responses to bacterial cyclic dinucleotides" Microbes and Infection vol. 14 pp. 188-197 doi:10.1016/j.micinf.2011.09.002 (Year: 2012).*
Communication (International Preliminary Report on Patentability) issued by the International Searching Authority in International Application No. PCT/US2018/033900 dated Nov. 26, 2019, 9 pages total.
Communication (International Search Report) issued by the International Searching Authority in International Application No. PCT/US2018/033900 dated Aug. 10, 2018, 3 pages total.
Communication (Written Opinion) issued by the International Searching Authority in International Application No. PCT/US2018/033900 dated Aug. 10, 2018, 8 pages total.
Communication (Extended European Search Report) issued by the European Patent Office in European Application No. 18806252.5 dated Jan. 2, 2021, 7 pages total.
De Jong SD, Basha G, Wilson KD, Kazem M, Cullis P, Jefferies W, Tam Y. The immunostimulatory activity of unmethylated and methylated CpG oligodeoxynucleotide is dependent on their ability to colocalize with TLR9 in late endosomes. The Journal of Immunology. 2010;184(11):6092-6102.

* cited by examiner

*Primary Examiner* — Eric Olson
(74) *Attorney, Agent, or Firm* — Troutman Pepper Hamilton Sanders LLP

(57) ABSTRACT

The invention relates to pharmaceutical compositions comprising mono- and/or oligonucleotides, dosage forms, and methods for treating and preventing diseases.

24 Claims, No Drawings

OLIGONUCLEOTIDE COMPOSITIONS AND METHODS FOR TREATING DISEASES

CROSS-REFERENCE TO RELATED APPLICATIONS

This application is a U.S. National Phase of International Patent Application No. PCT/US2018/033900, filed May 22, 2018, which published as WO 2018/217756 A1 on Nov. 29, 2018, and claims priority to U.S. Provisional Application Ser. No. 62/510,461, filed on May 24, 2017, the contents of which are incorporated herein by reference in their entirety.

FIELD OF THE INVENTION

The invention relates to pharmaceutical compositions comprising mono- and/or oligonucleotides, dosage forms, and methods for treating and preventing diseases.

BACKGROUND OF THE INVENTION

Known methods of treating human diseases of unknown etiology include the use of corticosteroids and other immunosuppressants, and cytostatics (C. Garnett, J. F. Apperley, and J. Pavlu, Treatment and management of graft-versus-host disease: improving response and survival, Adv Hematol. 2013; 4(6): 366-378); alkylating agents, and antimetabolites (DJ. Black and RB. Livingston, Antineoplastic Drugs, Review (Part 1) Drugs, 1990, 39 (4): 489-501), among others. Various synthetic oligonucleotides are under study as anti-tumor substances, immunostimulatory drugs, and potential therapies for treating viral diseases and muscular dystrophy.

Although oligonucleotides have been regarded as a new class of drugs for more than three decades, their therapeutic applications have so far failed to fully live up to the expectations. Today, there are many different subclasses of oligonucleotides, grouped mainly by different mechanisms of biological action, and include antisense, splice-switching oligonucleotides, siRNA, miRNA, aptamers and immunostimulatory oligonucleotides. Structural differences are minimal, and consequently all nucleic acid based drugs generally suffer from poor pharmacokinetics (J. Winkler, Oligonucleotide conjugates for therapeutic applications, Ther Deliv, 2013, 4(7), 791-809). Among registered drugs, Mipomersen is known (McGowan M P, TardifJ-C, Ceska R, et al. Randomized, placebo-controlled trial of mipomersen in patients with severe hypercholesterolemia receiving maximally tolerated lipid-lowering therapy. PLoS ONE. 2012; 7(11):e49006; Gelsinger C, Steinhagen-thiessen E, Kassner U. Therapeutic potential of mipomersen in the management of familial hypercholesterolaemia. Drugs. 2012; 72(11): 1445-1455; Parhofer K G. Mipomersen: evidence-based review of its potential in the treatment of homozygous and severe heterozygous familial hypercholesterolemia. Core Evid. 2012; 7:29-38).

Diseases of unknown etiology, for which many explanations have been proposed, include, among others, various dissimilar diseases and conditions, in particular, schizophrenia, oncological diseases, graft versus host reaction, myocardial infarction, stroke, autism, neurodegenerative diseases (Alzheimer's disease, Parkinson disease, dementia, etc.), acute interstitial nephritis, hypertensive crises, aging, bipolar disorder, multiple sclerosis, amyotrophic lateral sclerosis, other demyelinating diseases of the central nervous system, ankylosing spondylitis, systemic lupus erythematosus, scleroderma, CADASIL Syndrome, Huntington's disease, depressive disorder, acute respiratory distress syndrome, Crohn's disease, thrombosis, cancer, cancer cachexia, gout, inflammatory bowel disease, ulcerative colitis, primary biliary cirrhosis, primary sclerosing cholangitis, and attempts to increase life expectancy, among others.

SUMMARY OF THE INVENTION

Bacterial chromosomal DNA contains a large number of methylated cytosine and adenine. For example, the DNA of E. coli contains 19,120 6-methyladenines and 12,045 5-methylcytosines in addition to the four regular bases (EcoSal Plus. 2014 May; 6(1): doi:10.1128/ecosalplus.ESP-0003-2013. DNA Methylation M. G. Marinusl,* and A. Løbner-Olesen).

Presently, it has been surprisingly discovered that a therapeutic effect can be achieved in a number of diseases, including, without limitation, oncological diseases (e.g., cancer), neurodegenerative disease (e.g., Alzheimer's Disease), stroke, and graft versus host disease, by introducing a mixture of oligonucleotides and mononucleotides with methylated components, e.g., 5-methylcytosine, 6-methyladenine, and other nucleotides methylated at various positions.

Accordingly, the object of the invention is to provide pharmaceutical compositions, dosage forms, and methods of treatment for diseases based on mixtures of mono-, oligo- and polynucleotides which comprise methylated nucleotides.

Various non-limiting aspects and embodiments of the invention are described below.

In one aspect, a method for treating a disease and/or condition in a patient in need of such treatment comprising administering to said patient a therapeutically effective amount of a mixture of mono- and/or oligonucleotides comprising methylated nucleotides is provided.

In one embodiment, the disease and/or condition to be treated is selected from the group consisting of schizophrenia, oncological diseases, graft versus host reaction, myocardial infarction, stroke, chronic fatigue syndrome, autism, neurodegenerative diseases selected from Alzheimer's disease, Parkinson disease, and dementia, acute interstitial nephritis, hypertensive crises, aging, bipolar disorder, multiple sclerosis, amyotrophic lateral sclerosis, other demyelinating diseases of the central nervous system, ankylosing spondylitis, systemic lupus erythematosus, scleroderma, CADASIL Syndrome, Huntington's disease, depressive disorder, acute respiratory distress syndrome, Crohn's disease, thrombosis, cancer, cancer cachexia, gout, inflammatory bowel disease, ulcerative colitis, primary biliary cirrhosis, primary sclerosing cholangitis, Hashimoto's thyroiditis, Alzheimer's diseases, Parkinson' diseases, Friedreich's ataxia, Lewy body diseases, and spinal muscular atrophy.

In another embodiment, the disease and/or condition to be treated is selected from the group consisting of oncological disease, neurodegenerative disease, stroke, and graft versus host disease.

In one embodiment, the disease is a tumor. In one embodiment, the disease is cancer. In one embodiment, the disease is Graft versus host disease. In one embodiment, the disease is an acute ischemic condition. In one embodiment, the disease is a stroke. In one embodiment, the disease is Alzheimer's disease.

In another aspect, a method of increasing a life span of a subject in need thereof is provided comprising administering to said subject an effective amount of a mixture of mono- and/or oligonucleotides comprising methylated nucleotides.

In one embodiment, the mixture of mon- and/or oligonucleotides is produced the mixture of mono- and/or oligonucleotides is produced by a nuclease treatment of polymeric DNA, wherein said DNA is selected from the group consisting of eukaryotic DNA, archaeal DNA, Gram-positive bacterial DNA, Gram-negative bacterial DNA, and fungal DNA.

In one embodiment, the mixture of mono- and/or oligonucleotides is produced by a nuclease treatment of polymeric DNA, wherein said DNA is extracellular DNA. In one embodiment, the mixture of mono- and/or oligonucleotides is produced by a nuclease treatment of polymeric DNA, wherein said DNA is genomic DNA.

In one embodiment, the nuclease may be selected from the group consisting of T7 Endonuclease I, Mung Bean Nuclease, Nuclease BAL-31, Nuclease P, Deoxyribonuclease IV, Deoxyribonuclease I, Deoxyribonuclease II, frequently cutting restriction enzymes, and any combinations thereof.

In one embodiment, the nuclease treatment is conducted for 12-20 hours at room temperature in the presence of Ca+ and Mg+ ions.

In one embodiment, the mono- and/or oligonucleotides in the mixture are obtained synthetically.

In one embodiment, the mixture of mono- and oligonucleotides comprises mononucleotides, di-, tri-, tetra- and pentanucleotides, and are essentially free of oligomers longer than 6 nucleotides.

In one embodiment, the mixture of mono- and oligonucleotides comprises 15-18% of mononucleotides.

In one embodiment, the mixture of mono- and oligonucleotides comprises methylated nucleotides. In one embodiment, the methylated nucleotides are methylated adenine and/or methylated cytosine.

In one embodiment, methylated adenine is present in an amount from 0.1% to 1% of the total nucleotide mixture. In one embodiment, methylated cytosine is present in an amount from 0.01% to 0.1% of the total nucleotide mixture.

In one embodiment, the mixture of mono- and/or oligonucleotides is administered parenterally, topically, transdermally, orally, by inhalation/pulmonary, vaginally, rectally, nasally, buccally, sublingually, subcutaneously, intradermally, intravenously, intramuscularly, intracranially, intravitreally, or intraperitoneally.

In one embodiment, the mixture of mono- and/or oligonucleotides is administered in combination with at least one compound that potentiates its activity.

In one embodiment, the mixture of mono- and/or oligonucleotides is administered as a composition which further comprises a pharmaceutically acceptable carrier or excipient.

In one embodiment, the subject is human.

In another aspect, a pharmaceutical composition comprising a mixture of mono- and/or oligonucleotides and a pharmaceutically acceptable carrier, is provided.

In one embodiment, the pharmaceutical composition comprising a mixture of mono- and/or oligonucleotides is effective for treating a disease selected from the group consisting of schizophrenia, oncological diseases, graft versus host reaction, myocardial infarction, stroke, chronic fatigue syndrome, autism, neurodegenerative diseases selected from Alzheimer's disease, Parkinson disease, and dementia, acute interstitial nephritis, hypertensive crises, aging, bipolar disorder, multiple sclerosis, amyotrophic lateral sclerosis, other demyelinating diseases of the central nervous system, ankylosing spondylitis, systemic lupus erythematosus, scleroderma, CADASIL Syndrome, Hunting-ton's disease, depressive disorder, acute respiratory distress syndrome, Crohn's disease, thrombosis, cancer, cancer cachexia, gout, inflammatory bowel disease, ulcerative colitis, primary biliary cirrhosis, primary sclerosing cholangitis in a patient in need of such treatment.

In one embodiment, the mixture of mono- and/or oligonucleotides is produced by a nuclease treatment of polymeric DNA, wherein said DNA is selected from the group consisting of eukaryotic DNA, archaeal DNA, Gram-positive bacterial DNA, Gram-negative bacterial DNA, and fungal DNA.

In one embodiment, the mixture of mono- and/or oligonucleotides is produced by a nuclease treatment of polymeric DNA, wherein said DNA is extracellular DNA. In one embodiment, the mixture of mono- and/or oligonucleotides is produced by a nuclease treatment of polymeric DNA, wherein said DNA is genomic DNA.

In one embodiment, the nuclease is selected from the group consisting of T7 Endonuclease I, Mung Bean Nuclease, Nuclease BAL-31, Nuclease P, Deoxyribonuclease IV, Deoxyribonuclease I, Deoxyribonuclease II, frequently cutting restriction enzymes, and any combinations thereof.

In one embodiment, the nuclease treatment is conducted for 12-20 hours at room temperature in the presence of Ca+ and Mg+ ions.

In one embodiment, the mono- and/or oligonucleotides in the mixture are obtained synthetically.

In one embodiment, the mixture of mono- and oligonucleotides comprises mononucleotides, di-, tri-, tetra- and pentanucleotides, and a negligible amount of oligomers longer than 6 nucleotides.

In one embodiment, the mixture of mono- and oligonucleotides comprises 15-18% of mononucleotides.

In one embodiment, the mixture of mono- and oligonucleotides comprises methylated nucleotides.

In one embodiment, the methylated nucleotides are methylated adenine and/or methylated cytosine.

In one embodiment, methylated adenine is present in an amount from 0.1% to 1% of the total nucleotide mixture.

In one embodiment, methylated cytosine is present in an amount from 0.01% to 0.1% of the total nucleotide mixture.

In one embodiment, the composition comprises one or more excipients selected from the group consisting of hypromellose, lactose monohydrate, carbopol, Polycarbophil, and starch-based gel.

In yet another aspect, a pharmaceutical dosage form comprising a mixture of mono- and/or oligonucleotides is provided.

In one embodiment, the pharmaceutical dosage form comprising a mixture of mono- and/or oligonucleotides is selected from a tablet, a pill, a powder, a lozenge, a sachet, a cachet, a dragee, an elixir, a suspension, an emulsion, a solution, a syrup, an aerosol (as a solid or in a liquid medium), nasal drops, oral drops, eye drops, an ointment, a cream, a lotion, a gel, a spray, a soft gelatin capsule, a hard gelatin capsule, a suppository, an enema, an encapsulated implant, a sterile injectable solution, and a sterile packaged powder.

DETAILED DESCRIPTION

Detailed embodiments of the present invention are disclosed herein; however, it is to be understood that the disclosed embodiments are merely illustrative of the invention that may be embodied in various forms. In addition, each of the examples given in connection with the various embodiments of the invention is intended to be illustrative, and not restrictive. Therefore, specific structural and functional details disclosed herein are not to be interpreted as limiting, but merely as a representative basis for teaching one skilled in the art to variously employ the present invention.

DEFINITIONS

Unless defined otherwise, all technical and scientific terms used herein have the same meaning as commonly understood by one of ordinary skill in the art to which this invention belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In a preferred embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

Mono- and/or Oligonucleotide Mixtures of the Invention

The mixtures of mono- and/or oligonucleotides of the invention can be produced synthetically or can be generated, for example, by treating polymeric DNA with different nucleases. Non-limiting examples of useful nucleases include, e.g., T7 Endonuclease I, Mung Bean Nuclease, Nuclease BAL-31, Nuclease P, Deoxyribonuclease IV, Deoxyribonuclease I, Deoxyribonuclease II, and frequently cutting restriction enzymes, e.g. EcoRI, HindIII, HaeIII, and the like.

In one embodiment, the mixtures of mono- and/or oligonucleotides comprise one or more mononucleotides and are substantially free of oligonucleotides. In another embodiment, the mixtures of mono- and/or oligonucleotides comprise one or more oligonucleotides and are substantially free of mononucleotides. In yet another embodiment, the mixtures of mono- and/or oligonucleotides comprise one or more mononucleotides and one or more oligonucleotides.

The mixtures of mono- and/or oligonucleotides may comprise the various nucleotides at any ratio. In one embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of mononucleotides to oligonucleotides. In another embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of mononucleotides to dinucleotides. In another embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of mononucleotides to trinucleotides. In another embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of mononucleotides to tetranucleotides. In another embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of mononucleotides to pentanucleotides.

In one embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of dinucleotides to trinucleotides. In one embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of dinucleotides to tetranucleotides. In one embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of dinucleotides to pentanucleotides.

In one embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of trinucleotides to tetranucleotides. In one embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of trinucleotides to pentanucleotides. In one embodiment, the mixtures of mono- and/or oligonucleotides may comprise a 1:1, or 1:2, or 1:3, or 1:4, or 1:5, or 1:6, or 1:10, or 1:20, or 1:50, or 1:100, or 1:500, or 1:1000, or 1:10,000, or 2:1, or 3:1, or 4:1, or 5:1, or 6:1, or 10:1, or 20:1, or 50:1, or 100:1, or 500:1, or 1000:1, or 10,000:1 ratio of tetranucleotides to pentanucleotides.

In one embodiment, the mixtures of mono- and/or oligonucleotides may comprise 0.0001% to 99.99% mononucleotides, 0.0001% to 99.99% dinucleotides, 0.0001% to 99.99% trinucleotides, 0.0001% to 99.99% tetranucleotides, 0.0001% to 99.99% of pentanucleotides, and less than 0.001% of oligomers longer than 6 nucleotides. In another embodiments, the mixtures of mono- and/or oligonucleotides may comprise 0.1% to 50% mononucleotides, 0.0001% to 20% dinucleotides, 0.0001% to 20% trinucleotides, 0.0001% to 20% tetranucleotides, 0.0001% to 20% of pentanucleotides, and less than 0.001% of oligomers longer than 6 nucleotides. In yet another embodiment, the mixtures of mono- and/or oligonucleotides may comprise 1% to 30% mononucleotides, 1% to 20% dinucleotides, 1% to 20% trinucleotides, 1% to 20% tetranucleotides, 1% to 20% of pentanucleotides, and less than 0.001% of oligomers longer than 6 nucleotides.

In one specific embodiment, the mixtures of mono- and/or oligonucleotides comprise 15-18% of mononucleotides, di-, tri-, tetra- and penta-nucleotides, and a negligible amount of oligomers longer than 6 nucleotides.

The mixtures can comprise methylated nucleotides, such as, e.g., methylated adenine and/or methylated cytosine. In one embodiment, methylated adenine is present in an amount of from 0.1% up to 1%, and methylated cytosine is present in an amount of from 0.01% up to 0.1% of the total nucleotide composition.

The mixtures of mono- and/or oligonucleotides may be derived from any DNA, including, without limitation, eukaryotic DNA, archaeal DNA, Gram-positive bacterial DNA, Gram-negative bacterial DNA, and fungal DNA, including both genomic and extracellular DNA.

Pharmaceutical Compositions and Dosage Forms

The present invention also provides pharmaceutical compositions comprising the mixtures of mon- and oligonucleotides described herein. When employed as pharmaceuticals, the mixtures of the invention can be administered in the form of pharmaceutical compositions which is a combination of the mixtures of the invention and a pharmaceutically acceptable carrier. These compositions can be prepared in a manner well known in the pharmaceutical art, and can be administered by a variety of routes. Such pharmaceutical compositions can be administered systemically. The term "systemic" as used herein includes parenteral, topical, transdermal, oral, by inhalation/pulmonary, vaginal, rectal, nasal, buccal, and sublingual administration. The term "parenteral" as used herein includes subcutaneous, intradermal, intravenous, intramuscular, intracranial, and intraperitoneal administration.

Pharmaceutical compositions containing the mixtures of mon- and oligonucleotides of the invention can be prepared in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of a tablet, a pill, a powder, a lozenge, a sachet, a cachet, a dragee, an elixir, a suspension, an emulsion, a solution, a syrup, an aerosol (as a solid or in a liquid medium), nasal drops, oral drops, an ointment, a cream, a lotion, a gel, a spray, a soft gelatin capsule, a hard gelatin capsule, a suppository, an enema, an encapsulated implant, a sterile injectable solution, and a sterile packaged powder.

In some embodiments, the pharmaceutical composition of the invention is in liquid form. Liquid forms include, by way of non-limiting example, emulsions, solutions, suspensions, syrups, slurries, dispersions, colloids and the like. In some embodiments, a pharmaceutical composition described herein is in liquid, semi-solid or solid (e.g., powder) form. In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, the pharmaceutical composition of the invention is a solid dosage form, such a tablet, a granule, a sachet, or a powder. Also provided are pharmaceutical compositions comprising a mixture of the invention in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in DPI).

In some embodiments, a composition is in a unit dose formulation for oral, intranasal, or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The mixtures of mono- and/or oligonucleotides of the invention can be effective over a wide dosage range and are generally administered in a pharmaceutically effective amount. It will be understood, however, that the amount of the mixture actually administered will usually be determined by a physician, according to the relevant circumstances, including the condition to be treated, the chosen route of administration, the actual mixture administered, the age, weight, and response of the individual patient, the severity of the patient's symptoms, and the like.

In some embodiments, the mixtures of mono- and/or oligonucleotides of the invention or compositions described herein are administered intranasally. As used herein, "nasal delivery-enhancing agents" include agents which enhance the release or solubility (e.g., from a formulation delivery vehicle), diffusion rate, penetration capacity and timing, uptake, residence time, stability, effective half-life, peak or sustained concentration levels, clearance and other desired nasal delivery characteristics (e.g., as measured at the site of delivery, or at a selected target site of activity) of the mixtures or compositions of the invention. Enhancement of mucosal delivery can thus occur by any of a variety of mechanisms, for example by increasing the diffusion, transport, persistence or stability of the mixtures or compositions of the invention, enzyme inhibition, increasing membrane fluidity, modulating the availability or action of calcium and other ions that regulate intracellular or paracellular permeation, solubilizing mucosal membrane components (e.g., lipids), changing non-protein and protein sulfhydryl levels in mucosal tissues, increasing water flux across the mucosal surface, modulating epithelial junctional physiology, reducing the viscosity of mucus overlying the mucosal epithelium, reducing mucociliary clearance rates, increasing nasal blood flow and other mechanisms. Suitable mucosal delivery enhancing agents will be clear to a person skilled in the art of pharmacology and are further described hereafter.

In addition to the mixtures of mono- and/or oligonucleotides of the invention, the nasal carrier and, optionally, one or more further additives and/or agents, the composition of the invention may further comprise one or more additional therapeutic ingredients (or active substances). These therapeutic ingredients can be any compound that elicits a desired activity or therapeutic or biological response in the subject. Non-limiting examples of useful additional therapeutic ingredients is provided in the Combination Treatments section, below.

The proportion of each further component in the nasal composition of the invention may vary depending on the components used. For example, but without being limiting, the amount of nasal carrier may be in the range of from 0.1 to 99.9% by weight of the total weight or volume of the composition. When present, the amount surfactant may be in the range from about 0.01 to about 10% or higher and preferably about 0.05 to about 1.0% by weight of the total volume or weight of the composition, the amount depending on the specific surfactant used. The amount is generally kept as low as possible since above a certain level no further enhancement of absorption can be achieved and also too high of a surfactant level may cause irritation of the nasal mucosa. The amount of delivery enhancing agents may be at least 0.1%, suitably in the range from about 0.5 to 10% of the total weight of the composition. Where the composition is liquid, the enhancing agent may suitably be present in an amount of from 0.1 to 5% w/v of the total composition. Preserving agents may be present in an amount of from about 0.002 to 0.02% by weight of the total weight or volume of the composition.

The useful delivery volume of the pharmaceutical compositions of the invention is limited by the size of the nasal cavity. Suitable delivery volumes will be clear to a person skilled in the art of pharmacology. Preferably, the total composition quantity administered at each nasal application comprises from about 0.02 to 0.5 ml, preferably about 0.07 to 0.3 ml, typically about 0.09-0.1 ml.

The present invention encompasses any delivery device that is suitable for nasal administration of the compositions of the invention. Preferably, such means administers a metered dosage of the composition. The composition of the present invention may be packed in any appropriate form or container as long as a means is provided to deliver the composition to the nasal mucosa. Non-limiting examples of useful intranasal delivery devices include, e.g., instillation catheters, droppers, unit-dose containers, squeeze bottles pump sprays, airless and preservative-fee sprays, compressed air nebulizers, metered-dose inhalers, insufflators and pressurized metered dose inhalers.

For administration of a liquid in drop form, compositions of the invention can be placed in a container provided with a conventional dropper/closure device, e.g. comprising a pipette or the like, preferably delivering a substantially fixed volume of composition/drop.

For administration of an aqueous solution as a nasal spray, the aqueous solution may be dispensed in spray form by a variety of methods known to those skilled in the art. For example, such compositions will be put up in an appropriate atomizing device, e.g. in a pump-atomizer, or the like. The atomizing device will be provided with appropriate means, such as a spray adaptor for delivery of the aqueous spray to the naris. Preferably it will be provided with means ensuring delivery of a substantially fixed volume of composition/ actuation (i.e. per spray-unit). Examples of nasal sprays include nasal actuators produced by Ing. Erich Pfeiffer GmbH, Radolfzell, Germany (see U.S. Pat. Nos. 4,511,069, 4,778,810, 5,203,840, 5,860,567, 5,893,484, 6,227,415, and 6,364,166. Additional aerosol delivery forms may include, e.g., compressed air-, jet-, ultrasonic-, and piezoelectric nebulizers.

Alternatively the spray may be bottled under pressure in an aerosol device. The propellant may be a gas or a liquid (e.g. a fluorinated and/or chlorinated hydrocarbon). The spray composition may be suspended or dissolved in a liquid propellant. Stabilizing and/or suspending agents and/or co-solvents may be present.

A dry powder may be readily dispersed in an inhalation device as described in U.S. Pat. No. 6,514,496 and Garcia-Arieta et al., Biol. Pharm. Bull. 2001; 24: 1411-1416.

If desired a powder or liquid may be filled into a soft or hard capsule or in a single dose device adapted for nasal administration. The powder may be sieved before filled into the capsules such as gelatin capsules. The delivery device may have means to break open the capsule. The powdery nasal composition can be directly used as a powder for a unit dosage form. The contents of the capsule or single dose device may be administered using e.g. an insufflator. Preferably it will be provided with means ensuring dosing of a substantially fixed amount of composition.

In another embodiment, the composition of the invention can be provided as a nasal insert having the mixture of the invention dispersed therein. The insert may be retained in the naris, but flushed by the nasal mucus, and may be designed to release the compound of the invention at the same place in the naris. Suitable nasal insert types include nasal plugs, tampons and the like. Further examples of nasal inserts, their characteristics and preparation are described in EP 490806.

In one aspect, a composition or unit dosage form according to the invention is formulated for sublingual administration, wherein the unit dosage form is a film including one or more disintegrants (e.g., materials that favor disintegration or fast dissolution by virtue of their solubility in water, such as hydrolyzed starches, sugars, and glycerin, which may play a dual role as a plasticizer and disintegrant) and a plasticizing agent, the film having a first portion including apomorphine hydrochloride, and a second portion including pH neutralizing agent, wherein the unit dosage form includes from 0.5 to 5 mg, from 4 to 10 mg, or from 8 to 20 mg of apomorphine hydrochloride and the pH neutralizing agent is present in an amount sufficient to produce a solution having a pH of between 3.0 and 6.0, preferably between 4.5 and 6.5, (e.g., a pH of between 2.5 and 4.5, 3.0 and 6.0, 3.5 and 6.5, 4.5 and 6.5, or 5.0 and 6.0) when the unit dosage form is placed in unbuffered water at pH 7 (e.g., the pH observed within 5 minutes of placing the unit dosage form in 1, 5, or 10 mL of unbuffered water). The film can include from 1 to 50% (w/w) (e.g., 1±0.75%, 2±1.5%, 3±0.5%, 5±2%, 7.5±2.5%, 10±2%, 14±3%, 18±4%, 22±5%, 25±5%, 30±5%, 35±5%, 40±5%, 45±5%, or 50±5% (w/w)) of the one or more disintegrants. In certain embodiments, the unit dosage form further includes a high molecular weight polymer having a weight average molecular weight of greater than 60 KDa selected from hydroxypropyl cellulose, hydroxypropyl methyl cellulose, hydroxyethyl cellulose, carboxymethyl cellulose, and methyl cellulose. In other embodiments, the unit dosage form further includes a low molecular weight polymer having a weight average molecular weight of from 5 KDa to 50 KDa selected from hydroxypropyl cellulose, hydroxypropyl methyl cellulose, hydroxyethyl cellulose, carboxymethyl cellulose, and methyl cellulose. The pH neutralizing agent can be an organic base (e.g., pyridoxine, meglumine, or any organic base described herein) or an inorganic base (e.g., magnesium hydroxide, sodium bicarbonate, or an inorganic base described herein). In particular embodiments, the unit dosage form includes 35±5% (w/w) disintegrant, from 0.5 to 5 mg, from 4 to 10 mg, or from 8 to 20 mg of apomorphine hydrochloride and pyridoxine present in an amount sufficient to produce a solution having a pH of between 4.5 and 6.5 when the unit dosage form is placed in unbuffered water at pH 7. Suitable film for oral administration of the compositions according to the invention is disclosed in, e.g., U.S. Pat. No. 8,846,074.

In some embodiments, a composition or unit dosage form described herein is administered as a tablet, a pill, a powder, a lozenge, a sachet, a cachet, a dragee, an elixir, a suspension, an emulsion, a solution, a syrup, an aerosol (as a solid or in a liquid medium), nasal drops, oral drops, an ointment, a cream, a lotion, a gel, a spray, a soft gelatin capsule, a hard gelatin capsule, a suppository, an enema, an encapsulated implant, a sterile injectable solution, and a sterile packaged powder, or the like. In certain aspects, about 0.000001 mg to about 2000 mg, about 0.00001 mg to about 1000 mg, or about 0.0001 mg to about 750 mg, about 0.001 mg to about 500 mg, about 0.01 mg to about 250 mg, about 0.1 mg to about 100 mg, about 0.5 mg to about 75 mg, about 1 mg to about 50 mg, about 2 mg to about 40 mg, about 5 mg to about 20 mg, or about 7.5 mg to about 15 mg of a mixture of mono- and/or oligonucleotides per day or per dose is administered to an individual.

In some embodiments, the mixture of the invention is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of corticosteroid administered daily or in a unit dose is between about 0.5 mg and about 3 mg, between about 0.5 mg and about 4 mg, or between about 0.35 mg and about 4 mg. In other embodiments, the amount of the mixture present in a unit dose or administered daily is between about 1 and about 3 mg, or between about 1 and about 2 mg, or between about 2 and about 3 mg.

In certain aspects, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of the mixture per day or per dose is administered to a patient.

In some embodiments, the mixture is present in a unit dose in an amount of between about 5 mg and about 500 mg. In some embodiments, the amount of the mixture administered daily or in a unit dose is between about 5 mg and about 300 mg. In other embodiments, the amount of the mixture present in a unit dose or administered daily is between about 5 and about 250 mg, or between about 5 and about 200 mg, between about 5 mg and about 150 mg, between about 5 mg and about 100 mg, or between about 5 and about 50 mg.

In preparing a formulation, the active mixture can be milled to provide the appropriate particle size prior to combining with the other ingredients. If the active mixture is substantially insoluble, it can be milled to a particle size of less than 200 mesh. If the active mixture is substantially water soluble, the particle size can be adjusted by milling to provide a substantially uniform distribution in the formulation, e.g. about 40 mesh. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid pre-formulation composition containing a homogeneous mixture of the invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.000001 to about 2000 mg of the active ingredient of the present application.

The tablets or pills containing the mixture of mono- and/or oligonucleotides can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the mixture of mono- and/or oligonucleotides and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases.

Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the nucleotide mixture preparations typically will be between 3 and 11, more preferably from 5 to 9. It will be understood that use of certain of the foregoing excipients, carriers, or stabilizers will result in the formation of pharmaceutical salts.

The therapeutic dosage of the mixtures of the invention can vary according to, for example, the particular use for which the treatment is made, the manner of administration of the mixture, the health and condition of the patient, and the judgment of the prescribing physician. The proportion or concentration of the mixture of mono- and/or oligonucleotides of the invention in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present application also includes pharmaceutical kits useful, for example, in the treatment of diseases, which include one or more containers containing a pharmaceutical composition comprising a therapeutically effective amount of the mixture of mono- and/or oligonucleotides of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the invention, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

Methods of Treatment

In one aspect, methods of treating a disease and/or condition in a patient in need of such treatment by administering to said patient a therapeutically effective amount of a mixture of mono- and/or oligonucleotides comprising methylated nucleotides are provided. In one embodiment, the disease and/or condition to be treated is selected from the group consisting of schizophrenia, oncological diseases, graft versus host reaction, myocardial infarction, stroke, autism, neurodegenerative diseases selected from Alzheimer's disease, Parkinson disease, and dementia, acute interstitial nephritis, hypertensive crises, aging, bipolar disorder, multiple sclerosis, amyotrophic lateral sclerosis, other demyelinating diseases of the central nervous system, ankylosing spondylitis, systemic lupus erythematosus, scleroderma, CADASIL Syndrome, Huntington's disease, depressive disorder, acute respiratory distress syndrome, Crohn's disease, thrombosis, cancer, cancer cachexia, gout, inflammatory bowel disease, ulcerative colitis, primary biliary cirrhosis, primary sclerosing cholangitis.

Non-limiting examples of diseases and conditions treatable by bacteriophage inhibition or inactivation according the methods of the present invention include, without limitation, diseases associated with changes in properties of microbiota (e.g., skin, mucosal, or GI microbiota); oncological diseases; obesity; age-related changes of skin; vaginosis, neurodegenerative diseases; Chronic Fatigue Syndrome, Obsessive-Compulsive Disorder, generalized anxiety disorder (GAD), major depressive disorder (MDD), social anxiety disorder (SAD), attention-deficit/hyperactivity disorder (ADHD); diseases and conditions accompanied by increased intestinal permeability (e.g., irritable bowel syndrome [IBS], non-specific ulcerative colitis, celiac disease, diabetes, rheumatoid arthritis, multiple sclerosis, Amyotrophic Lateral Sclerosis [ALS], CADASIL Syndrome, Huntington's disease, stroke, psoriasis, Sudden arrhythmic death syndrome, diabetes, Crohn's disease, atopic dermatitis, ankylosing spondylitis, bipolar disorder, depressive disorder, schizophrenia, carcinogenesis, psoriasis, systemic lupus erythematosus [SLE], scleroderma, liver failure, liver cirrhosis, unstable angina, chronic heart failure, atherosclerosis, myocardial infarction, thrombosis, gout, cancer cachexia, acute respiratory distress syndrome, graft-versus-host reactions, rhythm and conduction disturbances, autism and autism spectrum disorder, primary biliary cirrhosis, primary sclerosing cholangitis, asthma; increase in life expectancy, Hashimoto's thyroiditis, Alzheimer's diseases, Parkinson' diseases, Friedreich's ataxia, Lewy body diseases, and spinal muscular atrophy).

In another embodiment, the disease and/or condition to be treated is selected from the group consisting of oncological disease, neurodegenerative disease, stroke, and graft versus host disease. In some embodiments, the disease and/or condition is cancer, for example colon cancer.

In yet another embodiment, a method of increasing lifespan of a subject is provided by administering to said subject an effective amount of a mixture of mono- and/or oligonucleotides comprising methylated nucleotides.

The methods of the invention may be used in a mammal, for example a human, of any age. In certain embodiments, the individual is an adult, for example an elderly person, for example a person over the age of 50, 55, 60, 65, or 70 years. In certain other embodiments, the individual is a child, for example an infant, or a child, or a teenager, for example a person under the age of 18, 16, 14, 12, 10, 8, 6, 4, 2, or 1 years of age.

Combination Treatment

In one embodiment of any of the above methods, the method further comprises administering a therapeutic or preventive treatment to the subject. Non-limiting examples of useful treatments include, for example, a vitamin, an antibiotic, an anti-tumor drug, a sorbent, a chitosan, an antiviral drug, an antibody, a pain reducer, an analgesic, an antipsychotic drug an antimutagen, a virus adsorption inhibitor, and other drugs currently used for the treatment of diseases listed above and combinations thereof.

In another embodiment, the method further comprises administering a mixture of nucleotides of the invention in combination with at least one compound that potentiates its activity.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Preparation of Methylated Mono- and/or Oligonucleotides

Bacteria grown on solid culture medium were washed with buffer, resuspended and purified by double reprecipitation at 5000 g. The resulting polymer in TE buffer had maximum absorption at 260 nm.

Bacterial DNA was isolated by the following two methods:

1) Phenol-chloroform extraction (*E. coli* Genomic DNA Extraction Fanglian He Vol 1, Iss 14, Jul. 20, 2011); or 2) The method for DNA isolation using the isolation kit for bacterial genomic DNA (GeneON. Molecular Biology, available at www.taq-dna.com/bacterial-dna-purification-_393.html).

Nucleic acids and proteins have absorbance maxima at 260 and 280 nm, respectively. Historically, the ratio of absorbance at these wavelengths has been used as a measure of purity in both nucleic acid and protein extractions. A ratio of ~1.8 is generally accepted as "pure" for DNA (Assessment of nucleic acid purity, Thermo Scientific, 2013, available at www.nanodrop.com/Library/T042-NanoDrop-Spectrophotometers-Nucleic-Acid-Purity-Ratios.pdf).

Preparation of Oligonucleotides.

Polymeric DNA was treated with different nucleases: T7 Endonuclease I, Mung Bean Nuclease, Nuclease BAL-31 (all from New England Biolabs), Nuclease P (Deoxyribonuclease IV, Deoxyribonuclease I, or Deoxyribonuclease II (all Sigma-Aldrich) for 12-20 hours at room temperature in the presence of Ca+ and Mg+ ions according to the manufacturers recommendations, followed by nuclease inactivation at 60-90° C. The inactivated nuclease was separated by ultrafiltration (10 KD Amicon Ultra).

TABLE 1

Types of oligomers generated by different DNases cutting.

| Test group | Mono- oligonucleotide* |
|---|---|
| 1 | 1 nucleotide |
| 2 | 2-4 nucleotides |
| 3 | 4-7 nucleotides |
| 4 | 8 and more |

The samples contained mono- (15-18%), di-, tri-, tetra- and penta-nucleotides. Amount of longer oligomers (6+ nucleotide) was negligible.

*Methylated adenine was present in an amount from 0.1% up to 1%, and methylated cytosine—from 0.01% up to 0.1%, as determined by Mass Spectrometry.

Example 2: Use of Mono- and/or Oligonucleotide Mixtures for Treatment of Tumors

Treatment of Colon Cancer

The studies were performed in male albino Wistar rats (Rappolovo breeding nursery), aged 14 weeks, weighing 180-190 g. Prior to the study period, animals (n=600) were kept in identical conditions, and received the same diet. For modeling colon cancer, the animals received Azoxymethane (Sigma) in the amount of 10 mg/kg (in 0.9% NaCl) for 12 weeks. In 26 weeks, the abdomen of anesthetized animals was opened, and the presence and size of colon tumors and metastases was visually assessed. Animals bearing neoplasms of more than 3 mm in diameter and having no observed metastases (360 animals) were subjected to total colectomy. In 2 days after surgery, mono- and/or oligonucleotide mixtures were administered either parenterally (via IV) or enterally (with drinking water). Each group consisted of 20 animals. In 8 weeks, surviving animals were sacrificed (animals were randomized into groups with 10 surviving animals per group), and the recurrence rates and presence of metastases was evaluated.

Enteral Administration The first control group received no treatment. Test group #1, Test group #2, Test group #3, Test group #4, Test group #5, and Test group #6 received mixtures of mono- and/or oligonucleotides (from 1 to 100,000 mcg/kg/day) prepared with the use of different nucleases, as specified in Table 2, below:

TABLE 2

Test groups of nucleotides used.

| Test groups | Nucleases used for Mono-oligonucleotide production |
|---|---|
| 1 | T7 Endonuclease I |
| 2 | Mung Bean Nuclease |
| 3 | Nuclease BAL-31 |
| 4 | Nuclease P |
| 5 | Deoxyribonuclease I |
| 6 | Deoxyribonuclease II |

The results are shown in Table 3

TABLE 3

| Group | No. of animals in the group with recurrences or metastases | No. of surviving animals/Total No. per group | No. of animals with metastasis |
|---|---|---|---|
| 1st control | 7 | 11/20 | 9 |
| 2nd control | 4 | 13/20 | 7 |
| Test group #1 | 3 | 17/20 | 2 |
| Test group #2 | 3 | 16/20 | 3 |
| Test group #3 | 4 | 17/20 | 2 |
| Test group #4 | 5 | 17/20 | 2 |
| Test group #5 | 2 | 18/20 | 1 |
| Test group #6 | 3 | 16/20 | 3 |

As Table 3 demonstrates, the number of animals with metastasis is lower across all test groups as compared to both control groups, which indicates that the mono- and/or oligotides are effective for the treatment of tumors.

Parenteral Administration (via IV)

The first control group received no treatment. The second control group received conventional therapy consisting of 5-fluorouracil (5 mg/kg/day). Test group #1, Test group #2, Test group #3, Test group #4, and Test group #5 were administered (from 1 to 100,000 mcg/kg/day for 30 days).

The results are shown in Table 4.

TABLE 4

| Group | No. of animals in the group with recurrences or metastases | No. of surviving animals/Total No. of animals per group | No. of animals with metastasis |
|---|---|---|---|
| 1st control | 8 | 10/20 | 8 |
| 2nd control | 4 | 14/20 | 6 |
| Test group #1 | 2 | 18/20 | 2 |
| Test group #2 | 1 | 17/20 | 0 |
| Test group #3 | 1 | 18/20 | 1 |
| Test group #4 | 2 | 17/20 | 1 |
| Test group #5 | 2 | 19/20 | 0 |

As Table 4 demonstrates, the number of animals with metastasis is lower across all test groups as compared to both control groups, which indicates that the mono- and/or oligotides are effective for the treatment of tumors.

Example 3: Use of Mono- and/or Oligonucleotide Mixtures for Increasing Life Span To evaluate the effect on lifespan, a fruit fly model was used.

Experimental Conditions.

Fruit flies were cultured in an incubator at 25° C. in 50 ml tubes containing 10 ml of Standard Yeast-Sugar Medium. For the experiment, adult insects were collected within 24 hours after molting; female and male flies were housed separately, 50 flies per tube, in tubes containing medium pretreated either with water (control), or with the experimental mono- and/or oligonucleotide mixtures. Flies were transferred to fresh medium twice a week. Dead flies were counted daily. The experiment was conducted in duplicate. Life span was analyzed by plotting Kaplan-Meier survival curves. Average life span, maximum life span, and median life span was calculated. The log-rank test and Wang-Allison test were used to compare survival curves and max life spans, respectively.

Treatment with experimental mixtures of mono- and/or oligonucleotides #1, 2, 3, 4, and 5, where these mixtures are as described above.

50 µl of the mono- and/or oligonucleotides mixtures according to the invention were applied to standard sugar-yeast culture medium and incubated without flies for 2 hours. The resulting nucleotide concentration was 0.032 mg/ml.

The effects of tested mono- and/or oligonucleotide mixtures on lifespan are summarized in Table 5.

TABLE 5

The effect of mixtures of mono- and/or oligonucleotides #1, 2, 3, 4, and 5 on *Drosophila melanogaster* D-32 lifespan.

| Group | N | ALS ± SE | MLS | Significance | M90 | M90-K |
|---|---|---|---|---|---|---|
| Females and males | | | | | | |
| Control | 435 | 37.6 ± 0.9 | 39.0 | — | 53 | |
| Test group #1 | 477 | 41.5 ± 0.8 | 43.0 | P < 0.05 | 58 | +9.4 |
| Test group #2 | 466 | 41.1 ± 0.8 | 42.0 | P < 0.01 | 58 | +9.4 |
| Test group #3 | 463 | 41.8 ± 1 | 41.0 | P < 0.05 | 57 | +7.5 |
| Test group #4 | 474 | 42.6 ± 0.6 | 44.0 | P < 0.05 | 59 | +11.1 |
| Test group 5 | 446 | 42.5 ± 0.7 | 44.0 | P < 0.05 | 59 | +11.1 |
| Males | | | | | | |
| Control | 480 | 32.7 ± 0.6 | 33.0 | | 43 | |
| Test group #1 | 477 | 35.8 ± 0.8 | 36.0 | P < 0.05 | 47 | +9.3 |
| Test group #2 | 474 | 36.3 ± 0.7 | 38.0 | P < 0.01 | 47 | +9.3 |
| Test group #3 | 446 | 37.1 ± 0.8 | 38.0 | P < 0.05 | 48 | +11.6 |
| Test group #4 | 463 | 35.1 ± 0.8 | 36.0 | P < 0.05 | 47 | +9.3 |
| Test group #5 | 463 | 34.9 ± 1.1 | 36.0 | P < 0.05 | 48 | +11.6 |

N is population size, ALS±SE: average lifespan±standard error of the mean (days); MLS: median lifespan (days); Significance is statistical significance when comparing survival curves of a certain group versus corresponding control group, the log-rank test, M90 is survival time of 90% population: max lifespan (days); M90-K is max lifespan difference from control, %.

As shown above, administration of the mono- and/or oligonucleotide mixtures of the present invention resulted in a statistically significant increase of median lifespan in female and male fruit flies. This geroprotective effect was identified for all oligonucleotides in the experimental groups #1, 2, 3, 4, and 5.

Example 4: Use of Mono- and/or Oligonucleotide Mixtures for Treatment of Graft Versus Host Diseases (GVHD)

To assess GVHD capabilities of the mono- and/or oligonucleotide mixtures, of the present invention were administered parenterally to mice.

White outbred mice (Rappolovo, St. Petersburg) aged 8 weeks, weighing 18-20 g were used in the experiment. The animals were subjected to gamma radiation at a dose of 1100-1200 Rad, with subsequent twice repeated intravenous administration of splenocytes at a total concentration of $10 \times 10^6$ cells. The resulting GVHD led to the death of 70% animals within 3 weeks. Each of the study groups consisted of 10 animals.

The first control group was administered 0.9% NaCl solution, mg, b.i.d., Test groups #1, 4 and 5 were administered via IV (from 1 to 100,000 mcg/kg/day), where the mixtures are as described above. The results are summarized in Table 6, below.

TABLE 6

| Group | No. of surviving animals in 3 weeks |
|---|---|
| 1st control group | 3 |
| Test group #1 | 8 |
| Test group #4 | 6 |
| Test group #5 | 9 |

Example 5: Use of Mono- and/or Oligonucleotide Mixtures for Treatment of Alzheimer's Disease In the first control group, the patients received conventional therapy, i.e., a reversible, noncompetitive glutamate receptors antagonist Memantine (10 mg per day). In the second control group the patients received placebo. Test group #4, and Test group #5 received compositions #4 and 5, respectively, in the form of extended release sublingual tablets (also comprising 12% hypromellose; 10% lactose monohydrate; 60% carbopol; 8% Polycarbophil; 10% starch-based gel) used 2 time a day. The patients were scored according to MMSE (Mini-Mental State Examination) and ADAScog (assessment of cognitive impairment) scales. 12 groups of 4 people were formed.

The results are shown in Table 7

TABLE 7*

| | Patients score | | | | | |
|---|---|---|---|---|---|---|
| | pre-treatment | | in 30 days | | in 90 days | |
| | MMSE | ADAScog | MMSE | ADAScog | MMSE | ADAScog |
| 1st control group | 13 | 41 | 15 | 37 | 16 | 37 |
| 2nd control group | 13 | 41 | 14 | 39 | 14 | 39 |
| Test group #4 | 13 | 41 | 16 | 36 | 17 | 35 |
| Test group #5 | 13 | 41 | 16 | 36 | 18 | 35 |

*Average values per group.

The above results demonstrate that the patients receiving compositions comprising mono- and/or oligonucleotides of the invention exhibit a significant improvement in their MMSE and ADAScog scores as compared to the group receiving conventional therapy.

Example 6: Use of Mono- and/or Oligonucleotide Mixtures for Treatment of Stroke in a Rat Model of Brain Ischemia To evaluate the efficacy of the mono- and/or oligonucleotide mixtures according to the invention in the treatment of stroke, a model of 10-15 min bilateral carotid arteries occlusion in the setting of systemic arterial hypotension up to 40 mm Hg in white rats (Rappolovo, Russia) was used (Smith M. L., Bendek G., Dahlgren N. et al., Models for studying long-term recovery—following forebrain ischemia in the rat. 2. A 2-vessel occlusion model/Acta Neurol. Scand. 1984. Vol. 69.—P. 385-401.). Evaluation of efficacy was based on the size of the necrosis area compared to a control. Necrosis area was stained with 0.25% thionin.

The animals in the control group received no treatment. Test group #3, Test group #4 received mono- and/or oligonucleotide mixtures #3-5, respectively, one minute prior to the impact (from 1 to 100,000 mcg/kg/day). Groups #3 and #4 additionally received Azithromycin (50 mg/kg/day) and Clarithromycin, respectively, (50 mg/kg/day). The results are summarized in Table 8, below.

TABLE 8

| Group | Necrosis area, compared to control (%) |
|---|---|
| Control | 100 |
| Test group #4 | 20 |
| Test group #5 | 17 |
| Test group #3 + Azithromycin | 14 |
| Test group #4 + Clarithromycin | 16 |

The mono- and/or oligonucleotide mixtures of the invention effectively reduced the necrosis area, as compared to the control, which indicates that they are effective for treating and preventing stroke.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

We claim:

1. A method for treating a disease in a subject in need of such treatment comprising administering to said subject a therapeutically effective amount of a mixture of mono- and oligonucleotides, wherein the mixture of mono- and oligonucleotides comprises mononucleotides, di-, tri-, tetra- and penta-nucleotides and is essentially free of oligonucleotides longer than 6 nucleotides, and wherein the disease is selected from a tumor, Graft versus host disease, a neurodegenerative disease, an acute ischemic condition, and stroke.

2. The method according to claim 1, wherein the tumor is cancer.

3. The method according to claim 1, wherein the neurodegenerative disease is Alzheimer's disease.

4. The method according to claim 1, wherein the mixture of mono- and/or oligonucleotides which is administered to the subject is a digest of polymeric DNA, wherein said DNA is selected from eukaryotic DNA, archaeal DNA, bacterial DNA, fungal DNA, and any combinations thereof.

5. The method according to claim 4, wherein said DNA is extracellular DNA.

6. The method according to claim 4, wherein the digest is a digest by a nuclease selected from T7 Endonuclease I, Mung Bean Nuclease, Nuclease BAL-31, Nuclease P, Deoxyribonuclease IV, Deoxyribonuclease I, Deoxyribonuclease II, frequently cutting restriction enzymes, and any combinations thereof.

7. The method according to claim 4, wherein the digestion is conducted for 12-20 hours at room temperature in the presence of Ca+ and Mg+ ions.

8. The method according to claim 1, wherein the mono- and/or oligonucleotides in the mixture are obtained synthetically.

9. The method according to claim 1, wherein the mixture of mono- and oligonucleotides comprises methylated nucleotides.

10. The method according to claim 9, wherein the methylated nucleotides are methylated adenine and/or methylated cytosine.

11. A method for treating a disease in a subject in need of such treatment comprising administering to said subject a therapeutically effective amount of a mixture of mono- and oligonucleotides, wherein the mixture of mono- and oligonucleotides comprises 15-18% of mononucleotides, and wherein the disease is selected from a tumor, Graft versus host disease, a neurodegenerative disease, an acute ischemic condition, and stroke.

12. A method for treating a disease in a subject in need of such treatment comprising administering to said subject a therapeutically effective amount of a mixture of mono- and oligonucleotides, wherein the mixture of mono- and oligonucleotides comprises methylated adenine and/or methylated cytosine, wherein methylated adenine is present in an amount from 0.1% to 1% of the total nucleotide mixture and/or wherein methylated cytosine is present in an amount from 0.01% to 0.1% of the total nucleotide mixture, and wherein the disease is selected from a tumor, Graft versus host disease, a neurodegenerative disease, an acute ischemic condition, and stroke.

13. A pharmaceutical composition comprising a mixture of mono- and oligonucleotides and a pharmaceutically acceptable carrier or excipient, wherein the mixture of mono- and oligonucleotides comprises mononucleotides, di-, tri-, tetra- and penta-nucleotides and is essentially free of oligonucleotides longer than 6 nucleotides.

14. The composition according to claim 13, wherein the mixture of mono- and oligonucleotides comprises 15-18% of mononucleotides.

15. The composition according to claim 13, wherein the mixture of mono- and oligonucleotides comprises methylated nucleotides.

16. The composition according to claim 15, wherein the methylated nucleotides are methylated adenine and/or methylated cytosine.

17. The composition according to claim 13, wherein the mixture of mono- and oligonucleotides is produced by a nuclease treatment of polymeric DNA, wherein said polymeric DNA is selected from eukaryotic DNA, archaeal DNA, bacterial DNA, fungal DNA, and any combinations thereof.

18. The composition according to claim 17, wherein said DNA is extracellular DNA.

19. The composition according to claim 17, wherein the nuclease treatment is conducted using a nuclease selected from T7 Endonuclease I, Mung Bean Nuclease, Nuclease BAL-31, Nuclease P, Deoxyribonuclease IV, Deoxyribonuclease I, Deoxyribonuclease II, frequently cutting restriction enzymes, and any combinations thereof.

20. The composition according to claim 17, wherein the nuclease treatment is conducted for 12-20 hours at room temperature in the presence of Ca+ and Mg+ ions.

21. The composition according to claim 13, wherein the mono- and/or oligonucleotides in the mixture are obtained synthetically.

22. The composition according to claim 13, wherein the carrier or excipient is selected from hypromellose, lactose monohydrate, carbopol, Polycarbophil, and starch-based gel.

23. A pharmaceutical dosage form comprising the pharmaceutical composition of claim 13.

24. A pharmaceutical composition comprising a mixture of mono- and oligonucleotides and a pharmaceutically acceptable carrier or excipient, wherein the mixture of mono- and oligonucleotides is essentially free of oligonucleotides longer than 6 nucleotides, wherein the mixture of mono- and oligonucleotides comprises methylated adenine and/or methylated cytosine, and wherein methylated adenine is present in an amount from 0.1% to 1% of the total nucleotide mixture and/or wherein methylated cytosine is present in an amount from 0.01% to 0.1% of the total nucleotide mixture.

\* \* \* \* \*